United States Patent [19]

Dinger, III et al.

[11] Patent Number: 5,376,078
[45] Date of Patent: Dec. 27, 1994

[54] ROTATABLE SURGICAL CUTTING INSTRUMENT WITH POSITIONALLY ADJUSTABLE WINDOW

[75] Inventors: Fred B. Dinger, III, Belleair; Jeffrey G. Roberts, Palm Harbor; A. Frank Trott, Largo, all of Fla.

[73] Assignee: Linvatec Corporation, Largo, Fla.

[21] Appl. No.: 986,060

[22] Filed: Dec. 10, 1992

[51] Int. Cl.⁵ .................................. A61B 17/32
[52] U.S. Cl. .......................... 606/170; 606/180; 604/22
[58] Field of Search ............ 606/180, 170, 171, 169, 606/167, 80, 79; 128/751; 604/22

[56] References Cited

U.S. PATENT DOCUMENTS

| | | | |
|---|---|---|---|
| 2,708,437 | 5/1955 | Hutchins | 128/751 |
| 4,646,738 | 3/1987 | Trott | 606/180 X |
| 4,923,441 | 5/1990 | Shuler | 604/22 |
| 5,061,238 | 10/1991 | Shuler | 604/22 |
| 5,152,744 | 10/1992 | Krause et al. | 606/180 |
| 5,160,318 | 11/1992 | Shuler | 604/22 |
| 5,217,478 | 6/1993 | Rexroth | 606/180 |

Primary Examiner—Tamara L. Graysay

[57] ABSTRACT

Angular positional adjustment relative to a handpiece is provided for a cutting window located at the distal end of an outer tube in an endoscopic surgical cutting instrument. A two-member hub assembly for the outer tube includes one hub member having a polygonal socket and a second hub member having a polygonal plug. Axial disengagement of the plug and socket permits relative rotation between them to provide alternative engagement positions. One hub member engages the handpiece while the other has the outer tube secured thereto, whereby changes in the angular engagement position between the hub members results in changes of the angular position of the cutting window relative to the handpiece.

21 Claims, 2 Drawing Sheets

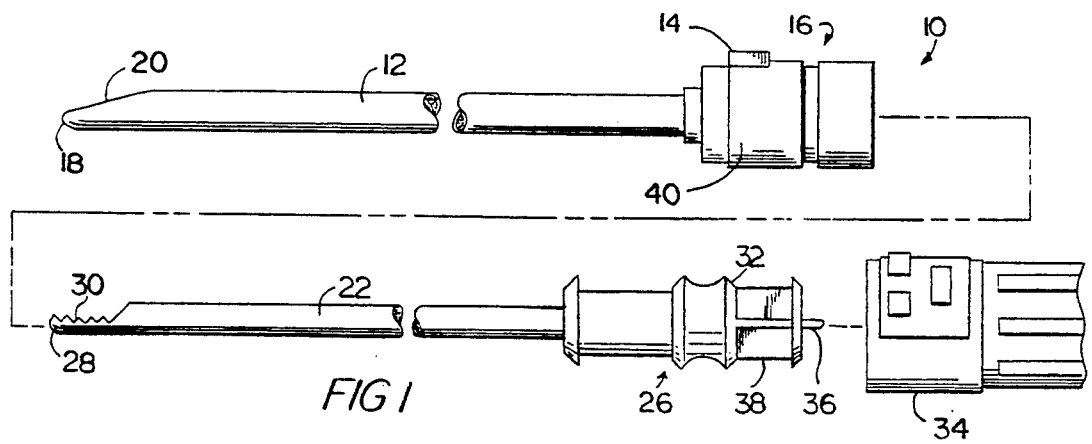
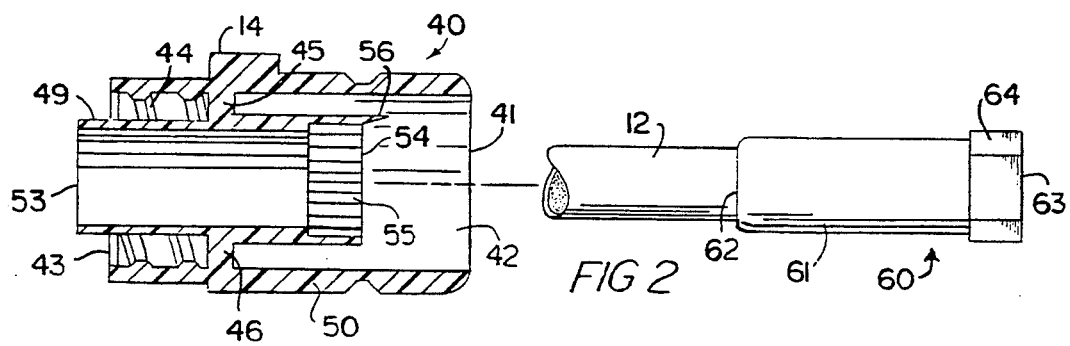
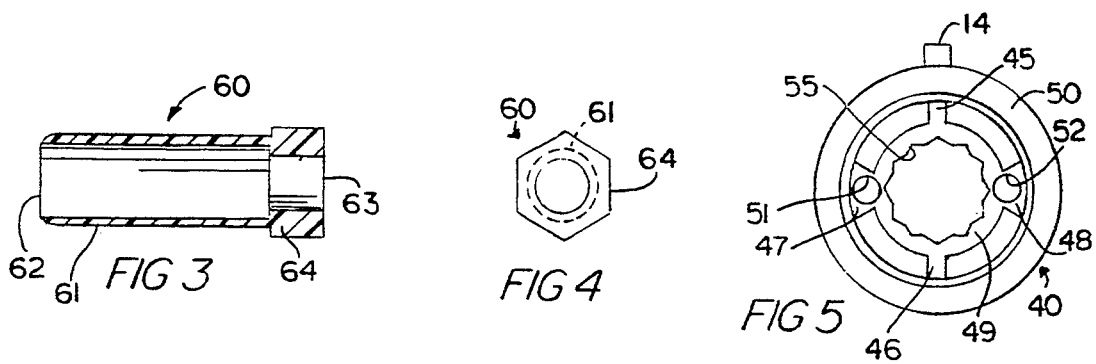
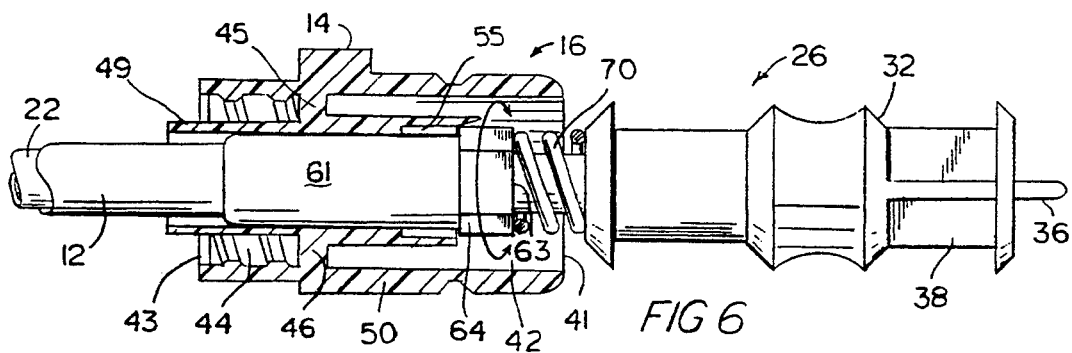

ROTATABLE SURGICAL CUTTING INSTRUMENT WITH POSITIONALLY ADJUSTABLE WINDOW

BACKGROUND OF THE INVENTION

Technical Field

The present invention pertains to surgical cutting instruments having relatively movable elongate inner and outer tubes arranged to cut tissue through a cutting window proximate the distal end of the outer tube. More particularly, the invention relates to improvements in selectively orienting the cutting window to facilitate utilization of the surgical instrument.

There is a genre of surgical instruments for use in closed, or endoscopic, surgery that are elongated to permit distal ends of the instruments to be positioned at internal surgical sites through one or more small portals cut into the patient's body. Examples of such instruments are found in U.S. Pat. No. 5,217,478 (Rexroth), U.S. Pat. No. 5,061,238 (Shuler) and U.S. Pat. No. 4,646,738 (Trott). The disclosures in all of these patents and patent application are expressly incorporated herein. Such surgical cutting instruments include relatively movable, cooperating, concentric inner and outer tubes elongated longitudinally so that the distal ends of the tubes can be positioned at internal surgery sites while their proximal ends are secured, externally of the patient's body, in a handpiece. The handpiece may contain a selectively actuable motor, or may transmit forces from an external motor, to rotate or otherwise move the inner tube relative to the fixed outer tube. At the distal end of the outer tube there is commonly formed a cutting opening or window to receive bodily tissue. The distal end of the inner tube is formed with a cutting surface or edge to engage the tissue through the cutting opening when the inner tube is moved relative to the outer tube. The cutting surface or edge of the inner tube cooperates with the cutting opening in the outer tube to shear, abrade or otherwise cut the tissue as the cutting surface moves past the cutting opening. In this regard, the cutting surface and the cutting opening may be configured as desired to produce a variety of cutting functions, such as whisker cutting, synovial resection, arthroplasty burring or abrading, side cutting, meniscus cutting, trimming, full radius resection and end cutting as appropriate for diverse types of tissue, such as soft tissue, cartilage and bone. The inner and outer tubes may be straight, or they may be bent at an angle suitable for a particular surgical application. Suction is normally produced through the handpiece and the lumen of the inner tube to permit cut tissue to be aspirated from the surgical site through the inner tube.

In the instruments described above, the outer tube has a plastic hub with a positioning tab keyed and retained in a corresponding slot in the handpiece. Since the outer tube is positionally fixed relative to its hub, the cutting window at the distal end of the inner tube is positionally fixed relative to the handpiece. The handpiece is typically designed to be held in the surgeon's hand in one optimum angular orientation about its axis, since the pushbutton motor controls on the handpiece must be positioned at the surgeon's finger tips. In many situations arising during surgery, the surgeon is required to either bend his or her wrist awkwardly, or rotate the handpiece to a position wherein the controls are not conveniently accessible, in order to position the cutting window properly at the surgical site.

OBJECTS AND SUMMARY OF THE INVENTION

It is therefore an objector the present invention to provide a method and apparatus for permitting a surgeon to adjustably position the cutting window in a surgical instrument of the type described without bending his or her wrist in an awkward manner or rotating the instrument handpiece so as to render the instrument controls inconvenient to operate.

It is another object of the present invention to permit selective positional adjustment of a cutting window relative to a handpiece in an endoscopic surgical instrument.

A further object of the invention is to permit the cutting window of an endoscopic surgical instrument to be selectively rotated to any of multiple angular positions relative to the instrument handpiece axis.

In accordance with the present invention, the hub of the outer tube of the surgical instrument is provided as two members adapted for mutual engagement in any of multiple angularly displaced positions. In a preferred embodiment, a first member of the outer hub includes a polygonal socket disposed coaxially about the outer tube axis. A second member of the outer hub includes a polygonal plug adapted to be received and engaged in the first member socket in any of multiple angularly displaced positions. The socket and plug may have the same polygonal configuration (e.g., each having n sides) wherein the number of angular positions corresponds to the number n of sides in each polygon. Alternatively, the plug polygon may include fewer sides than the socket polygon with the polygon being sized to retain the plug in the socket in as many angular positions as there are sides in the socket. In a preferred embodiment, there are twelve sides to the socket polygon (i.e., dodecagonal) and six sides in the plug polygon (i.e., hexagonal).

To adjust the angular position of the cutting window, the socket and plug are axially separated to permit rotation of the outer tube and its attached hub member relative to the other hub member attached to the handpiece until the cutting window is desirably positioned. The two members of the outer hub are then moved axially together to teengage the plug and socket in the desired angular position. The two members of the outer hub may be resiliently biased along their axes toward one another so that adjustment of the window requires holding the hub member attached to the outer tube in an axially displaced position in opposition to the bias force. Upon release of the outer tube, the bias force moves the two hub members axially into engagement.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 1 is an exploded side view of an endoscopic surgical instrument utilizing the features of the present invention.

FIG. 2 is an exploded side view in partial section illustrating a two-member hub construction for the outer tube in the instrument of FIG. 1.

FIG. 3 is a side view in section of the interior hub member of FIG. 2.

FIG. 4 is an end view of the interior hub member of FIG. 3.

FIG. 5 is an end view of the exterior hub member of FIG. 2.

FIG. 6 is a side view in partial section of an alternative embodiment of the present invention.

DESCRIPTION OF THE PREFERRED EMBODIMENTS

Figure 5A:
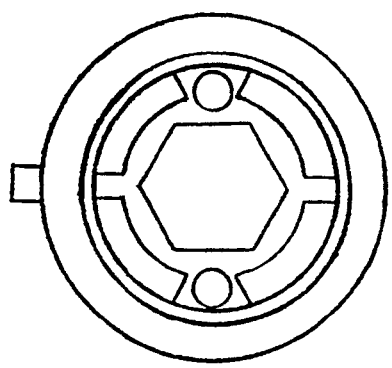
FIG. 5a is a schematic end view of a modified form of the exterior hub member of FIG. 2.

Referring specifically to FIG. 1 of the accompanying drawings, a surgical cutting instrument 10 includes an elongate hollow outer tubular member 12, typically made of stainless steel, having a proximal end fixedly secured to a hub 16, typically made of plastic. A distal end 18 of outer tube 12 has a cutting opening or window 20 defined therein. An elongate hollow inner tubular member 22, also typically made of stainless steel, is rotatably received in outer tube 12. The proximal end of inner tube 22 is fixedly secured to a hub 26, typically made of plastic configured to be received in the proximal end of hub 16 when inner tube 22 is coaxially disposed within outer tube 12. The distal end 28 of inner tube 22 has a cutting edge 30 formed thereon in a position to be juxtaposed with cutting window 20 when inner tube 22 is fully inserted into outer tube 12. In this position of the tubes, cutting edge 30 is able to engage bodily tissue through the cutting window as inner tube 22 rotates within outer tube 12.

Hub 26 has a central portion 32 with a transversely extending passage (not shown) extending therethrough. Inner tube 22 extends through an axial bore in hub 26 to intersect and provide flow communication with the transverse passage. A driven tang 36 extends rearwardly from a proximal portion 38 of hub 26 and is adapted to be driven by a rotating slotted drive shaft of an electric motor (not shown) in a handpiece 34. The structure of hub 26 is described herein only in brief general terms in view of the fact that it is the same hub provided for the inner tube in INTRA ARC cutting blades manufactured by Linvatec Corporation (Concept Division) and designed for use with the Concept INTRA ARC Model 9930 Arthroscopic Drive System and the Concept Model 9950F Handpiece.

Figure 7:
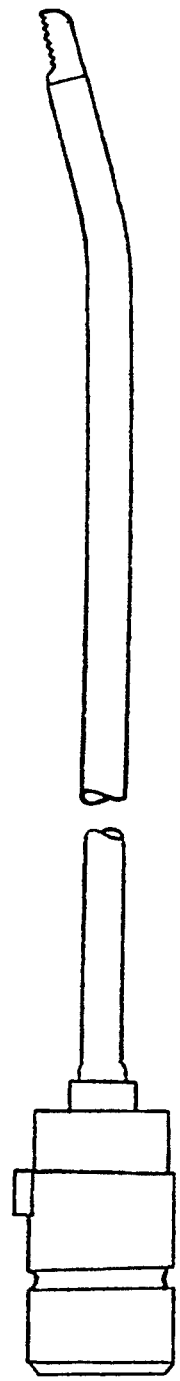
FIG. 7 is a schematic view in plan of a modified configuration of the instrument of the present invention.

Cutting window 20 in the distal end 18 of outer tube 12 extends along the side and end walls of the tube to provide a cutting edge surrounding the window. This cutting edge is described in greater detail in the above-referenced Shuler patent. The window cutting edge cooperates with cutting edge 30 of inner tube 22 to form a meniscus cutter in the illustrated embodiment. Window 20 can have any desired configuration to cooperate with the configuration of cutting edges on inner tube 22; for example, various cutting tip designs of the Concept INTRA ARC blade system may be employed to provide trimmers, end cutters, side cutters, full radius resectors, synovial resectors, whiskers, open end cutters, arthroplasty burrs, slotted whiskers, tapered burrs, oval burrs and punch forceps. While the surgical cutting instrument of the present invention is shown and described for use in the Concept INTRA ARC system, it will be appreciated that the instrument can have any desirable hub configuration to be utilized with any drive system or handpiece capable of rotating or reciprocating an elongate inner tubular member within an elongate outer tubular member to cut or otherwise engage bodily tissue at the distal end and aspirate cut tissue through the lumen of the inner tubular member. It will also be appreciated that the instrument of the present invention may be provided with its outer tube bent at a predetermined angle proximally of the distal end (see FIG. 7) in the manner described in the above-referenced Trott patent.

As described herein, prior art cutting blade assemblies suffer from the disadvantage of having a fixed orientation between the handpiece 34 and cutting window 20. This is so because the proximal end of hub 16 of outer tube 12 is received in handpiece 34 and positionally keyed therein by means of tab 14 extending radially from the hub. With hub 16 precluded from axial and rotational movement relative to the handpiece, the orientation of cutting window 20 in prior art instruments is likewise precluded from moving axially or rotationally relative to the handpiece. In accordance with the present invention, however, hub 16 is provided as two separate parts or members to permit different relative angular positions between them and, thereby, permit cutting window 20 to be oriented in multiple angular positions relative to handpiece 34. This two-part hub structure is described in detail below in relation to FIGS. 2–5.

Referring now to FIGS. 2–5, the outer tube hub 16 includes an exterior member 40 serving as a fixed hub portion, and an engagement or interior member 60, both made of suitable plastic material such as polycarbonate. Exterior hub member 40 has a generally cylindrical outer wall 50 which, at its proximal end 41, is open to define a proximal bore section 42. The distal end 43 of wall 50 is similarly open to define a distal bore section 44, the cylindrical inner wall of which is threaded to receive and engage a cannula (not shown) used to maintain the surgical instrument properly oriented through a portal in the patient's body.

A first pair of support ribs 45, 46 projects radially inward from cylindrical wall 50 at 180°-spaced angular locations at the interior extremity of bore section 42. Another pair of support ribs 47, 48 projects radially inward from wall 50 at 180°-spaced angular locations equidistant from ribs 45, 46. Ribs 45, 46, 47 and 48 support a generally cylindrical interior guide 49 in coaxial orientation and in spaced relation with respect to wall 50. Ribs 47, 48 also serve as supports for respective coding magnets (not shown) and are provided with respective magnet-receiving longitudinally extending bores 51, 52. In this regard, ribs 47, 48 are considerably longer than ribs 45, 46 (i.e., along the axial dimension of member 40) to accommodate the length of bores 51, 52 in bore section 42. In addition, ribs 47, 48 are wider than ribs 45, 46 (i.e., in the angular dimension about the axis of member 40) to accommodate the diameter of bores 51, 52. The coding magnets are utilized in the manner described in the above-referenced Rexroth patent application to identify the cutting blade assembly by type to sensors in the handpiece 34, thereby establishing the optimum operating speed range for the driving motor.

Guide 49 has a distal end 53 projecting forwardly beyond the open distal end 43 of wall 50. The proximal end 54 of guide 49 terminates within bore section 42 and has a polygonal socket or locking member 55 defined in its interior surface concentrically about the central longitudinal axis of wall 50. In the preferred embodiment of the invention, socket 55 is a regular twelve-sided polygon (i.e., a dodecagon), although, as described below, this is not a limiting configuration for the socket.

The axial length of socket 55 is typically on the order of twenty percent of the total axial length of guide 49. For the remainder of its length, the interior of guide 49 is a smooth cylinder having an inside diameter larger than the outside diameter of outer tube 12 and sized to slidably receive interior member 60 in the manner described below. A rib 56 projects rearwardly from the proximal end 54 of guide 49 to engage an interlock switch in handpiece 34, thereby to assure that the handpiece motor cannot be operated unless the cutting blade assembly is properly locked into the handpiece.

Interior member 60 of outer hub 16 takes the form of an elongate hollow cylinder 61 having an outer diameter sized to be slidably received in guide 49. Outer tube 12 is secured in and extends forwardly from the distal end 62 of cylinder 61. At the proximal end 63 of cylinder 61 there is a polygonal plug fitting or locking member 64 having its outside surface adapted to be received in polygonal socket or locking member 55 in multiple angular orientations. In the preferred embodiment of the invention, plug 64 is a regular hexagon with a maximum outside diameter (i.e., the diameter between opposite intersections of its sides) substantially equal to or just slightly smaller than the maximum inside diameter of socket 55. With this configuration, plug 64 can be fixed or locked in twelve different angular positions relative to socket 55. It will be appreciated that the invention is not limited to a hexagonal plug and dodecagonal socket; rather, any polygonal configurations providing angular adjustability between members 40 and 60 will serve the intended purpose. Moreover, the plug and socket need not have different numbers of sides; that is, for example, the plug and socket may both be hexagons (see FIG. 5a), octagons, etc.

When interior hub member 60 is fully inserted into exterior hub member 40, plug 64 is engaged in socket 55, and cylinder 61 extends distally into guide 49. Outer tube 12 thus projects distally from both guide 49 and outer hub 16, as best illustrated in FIG. 6. In order to change the angular orientation of cutting window 20 relative to handpiece 34, outer tube 12 is first pushed in a proximal direction relative to external member 40 until plug 64 and socket 55 are disengaged. Tube 12 is rotated about its axis until cutting window 20 faces in the desired angular direction, whereupon tube 12 can be pulled distally relative to member 40 until the plug and socket re-engage.

As illustrated in FIG. 6, a helical spring 70 may be disposed about inner cutting tube 20 at a location between the proximal end 63 of hub member 60 and the distal end of hub 26. Spring 70 serves to axially bias hub member 60 toward hub member 40, thereby biasing plug 64 toward socket 55. The bias serves to minimize inadvertent disengagement of members 40 and 60. To adjust the cutting window position when spring 70 is present, one would proceed as described above but would also maintain a continuous axial force between outer tube 12 and hub member 40 to keep the plug and socket axially separated while the tube 12 and its window 20 are rotated to the desired position.

The preferred embodiment of the invention has been described as utilizing a polygonal plug and socket arrangement to provide discrete angular positions of the cutting window relative to the handpiece axis. It will be appreciated by those skilled in the art that there are numerous other mechanisms and arrangements for achieving the same result, and such mechanisms and arrangements clearly fall within the scope of the invention. For example, one or more radially extending tabs or projections may be secured to one of the interior and exterior hub members to engage corresponding slots or receptacles disposed circumferentially about the other of the hub members. Moreover, it will be appreciated that the positioning of the plug on the interior hub member and the socket on the exterior hub member may be reversed.

From the foregoing description it will be appreciated that the invention permits angular positional adjustment of a cutting window relative to the handpiece in an endoscopic surgical cutting instrument.

Having described preferred embodiments of a new and improved rotatable surgical cutting instrument with positionally adjustable window constructed in accordance with the present invention, it is believed that modifications, variations and changes will be suggested to persons skilled in the art in view of the disclosures set forth herein. Accordingly, it is to be understood that all such variations, modifications and changes are believed to fall within the scope of the present invention as defined by the appended claims.

What is claimed is:

1. A surgical cutting instrument comprising:
   an inner tube having proximal and distal ends with a cutting means disposed proximate said distal end;
   an outer tube disposed in sheath-like fashion about said inner tube and having proximal and distal ends, said outer tube having a cutting window defined proximate its distal end in a position to permit said cutting means, when moving relative to said cutting window, to cut bodily tissue;
   drive means for cyclically moving said inner tube relative to said outer tube to thereby cyclically move said cutting means relative to said cutting window;
   a handpiece adapted to be grasped by a surgeon using said instrument; and
   an outer tube hub assembly secured at the proximal end of said outer tube and including means for selectively engaging said handpiece and preventing movement of said outer tube relative to said handpiece during said cyclical movement of said inner tube relative to said outer tube, said outer tube hub assembly including a positionally adjustable connection permitting selective angular positioning of said outer tube and said cutting window at plural discrete angular positions relative to said handpiece.

2. The surgical cutting instrument according to claim 1 wherein said outer tube hub assembly comprises:
   a first hub member having a proximal end including said means for engaging said handpiece; and
   a second hub member secured to the proximal end of said outer tube;
   wherein said connection includes an angularly adjustable engagement between said first and second hub members.

3. A surgical cutting instrument comprising:
   an inner tube having proximal and distal ends with a cutting means disposed proximate said distal end;
   an outer tube disposed in sheath-like fashion about said inner tube and having proximal and distal ends, said outer tube having a cutting window defined proximate its distal end in a position to permit said cutting means, when moving relative to said cutting window, to cut bodily tissue;

drive means for cyclically moving said inner tube relative to said outer tube to thereby cyclically move said cutting means relative to said cutting window;

a handpiece adapted to be grasped by a surgeon using said instrument;

an outer tube hub assembly secured at the proximal end of said outer tube and selectively engageable by said handpiece to prevent movement of said outer tube relative to said handpiece during said cyclical movement of said inner tube relative to said outer tube, said outer tube hub assembly including a positionally adjustable connection permitting selective angular positioning of said outer tube and said cutting window relative to said handpiece;

wherein said outer tube hub assembly comprises:

a first hub member having a proximal end adapted to engage said handpiece;

a second hub member secured to the proximal end of said outer tube;

wherein said connection includes an angularly adjustable engagement between said first and second hub members; and wherein said connection further comprises:

a polygonal socket defined in one of said hub members;

a polygonal plug defined in the other of said hub members;

wherein said plug is axially insertable into said socket in a plurality of alternative angular orientations in which angular movement between the hub members is precluded.

4. The surgical cutting instrument according to claim 3 wherein said polygonal socket has more sides than said polygonal plug.

5. The surgical cutting instrument according to claim 4 wherein said socket is a dodecagon and said plug is a hexagon.

6. The surgical cutting instrument according to claim 3 wherein said polygonal socket and said polygonal plug have the same number of sides.

7. The surgical cutting instrument according to claim 3:

wherein said first hub member is an exterior hub member having a hollow cylindrical guide with open proximal and distal ends;

wherein said second hub member is a generally cylindrical interior hub member having proximal and distal ends;

wherein the proximal end of said outer tube is secured to the distal end of said interior hub member;

wherein said polygonal socket is defined in said guide;

wherein said polygonal plug is defined in said interior hub member; and wherein said interior hub member is disposed for limited axial movement within said guide to permit selective engagement and disengagement between said plug and socket with said outer tube projecting distally from said exterior hub member.

8. The surgical cutting instrument according to claim 7 wherein said polygonal socket is defined at the proximal end of said guide, and wherein said polygonal plug is defined at the proximal end of said interior hub member.

9. The surgical cutting instrument according to claim 8 wherein said polygonal socket has more sides than said polygonal plug.

10. The surgical cutting instrument according to claim 9 wherein said socket is a dodecagon and said plug is a hexagon.

11. The surgical cutting instrument according to claim 8 wherein said polygonal socket and said polygonal plug have the same number of sides.

12. The surgical cutting instrument according to claim 8 further comprising a spring for resiliently axially biasing said plug and said socket into engagement.

13. The surgical cutting instrument according to claim 7 further comprising an inner tube hub assembly secured to the proximal end of said inner tube and adapted to be removably connected to drive means, said inner tube hub assembly including a forward end portion configured to be received in said outer tube hub assembly with said inner tube projecting through said outer tube.

14. The surgical cutting instrument according to claim 13 further comprising a spring disposed between said inner tube hub assembly and said interior hub member for resiliently axially biasing said plug and socket into engagement.

15. The surgical cutting instrument according to claim 3 wherein said outer tube is bent at a predetermined angle proximally of its distal end.

16. The surgical cutting instrument according to claim 3 further comprising a spring for resiliently axially biasing said plug and said socket into engagement.

17. A method for selectively orientating a cutting window relative to a handpiece in an endoscopic surgical cutting instrument of the type having an inner tube with a cutting edge at its distal end and movable within an outer tube having the cutting window at its distal end, said method comprising the steps of:

providing a two-member hub assembly for said outer tube;

connecting a first member of said hub assembly to said handpiece;

connecting a second member of said hub assembly to the proximal end of said outer tube; and selectively engaging said first and second hub members in multiple alternative mutual angular orientations;

whereby said cutting window has a different angular orientation relative to the axis of said handpiece in each of said multiple angular orientations.

18. The method according to claim 17 wherein the step of selectively engaging includes:

engaging a polygonal socket, formed on one of said members, with a polygonal plug formed on the other of said members; and providing for limited axial displacement between said socket and plug to permit temporary disengagement and relative rotation therebetween.

19. A surgical cutting instrument comprising:

a longitudinally extending, rotatable inner tube having a proximal end and a distal end, said inner tube provided with a cutting means adjacent said distal end;

an outer tube having an inside diameter substantially equal to the outside diameter of said inner tube, said outer tube having a proximal end and a distal end, the distal end of said outer tube being provided with a window opening adapted to enable said cutting means to cut tissue;

rotation means for rotating said inner tube within said outer tube, said rotation means connected to the proximal end of said inner tube;

an outer tube hub means connected to the proximal end of said outer tube;

a handpiece for holding said outer tube hub means, said window opening having a predetermined angular position relative to said handpiece; and adjusting means for selectively varying the angular position of said window relative to said hub means.

20. A surgical cutting instrument according to claim 19 wherein said adjusting means comprises:

a fixed hub portion having a proximal end releasably connectable to said handpiece, and a distal end having an axially aligned aperture for receiving the proximal end of said outer tube;

an engagement member formed at the proximal end of said outer tube;

a socket formed into said fixed hub portion and adapted to receive said engagement member to prevent rotation of said outer tube relative to said socket; and means for selectively retaining said outer tube within said socket whereby said window In the distal tip of said outer tube may be directed in any one of a plurality of discrete angular orientations.

21. A surgical cutting instrument according to claim 19 wherein said adjusting means comprises:

a fixed hub portion having a proximal end releasably connectable to said handpiece and a distal end having an axially aligned aperture for receiving the proximal end of said outer tube;

a first locking member secured proximate the proximal end of said outer tube;

a second locking member disposed on said fixed hub portion and adapted to engage said first locking member to prevent rotation of said outer tube relative to said fixed hub portion; and means for selectively retaining said outer tube within said aperture with said first and second locking member engaged, whereby said window in the distal tip of said outer tube may be directed in any one of a plurality of discrete angular orientations relative to said handpiece,

* * * * *

REEXAMINATION CERTIFICATE (3242nd)
United States Patent [19]
Dinger, III et al.

[11] B1 5,376,078
[45] Certificate Issued Jun. 24, 1997

[54] ROTATABLE SURGICAL CUTTING INSTRUMENT WITH POSITIONALLY ADJUSTABLE WINDOW

[75] Inventors: Fred B. Dinger, III, Belleair; Jeffrey G. Roberts, Palm Harbor; A. Frank Trott, Largo, all of Fla.

[73] Assignee: Linvatec Corporation, Largo, Fla.

Reexamination Request:
No. 90/003,968, Sep. 13, 1995

Reexamination Certificate for:
Patent No.: 5,376,078
Issued: Dec. 27, 1994
Appl. No.: 986,060
Filed: Dec. 10, 1992

[51] Int. Cl.$^6$ ................................................. A61B 17/32
[52] U.S. Cl. ........................ 606/170; 606/180; 604/22
[58] Field of Search ....................... 604/19, 22; 606/1, 606/79, 80, 167, 170, 179, 180

[56] References Cited

U.S. PATENT DOCUMENTS 3,618,611  11/1971  Urban .

*Primary Examiner*—Glenn Dawson

[57] ABSTRACT

Angular positional adjustment relative to a handpiece is provided for a cutting window located at the distal end of an outer tube in an endoscopic surgical cutting instrument. A two-member hub assembly for the outer tube includes one hub member having a polygonal socket and a second hub member having a polygonal plug. Axial disengagement of the plug and socket permits relative rotation between them to provide alternative engagement positions. One hub member engages the handpiece while the other has the outer tube secured thereto, whereby changes in the angular engagement position between the hub members results in changes of the angular position of the cutting window relative to the handpiece.

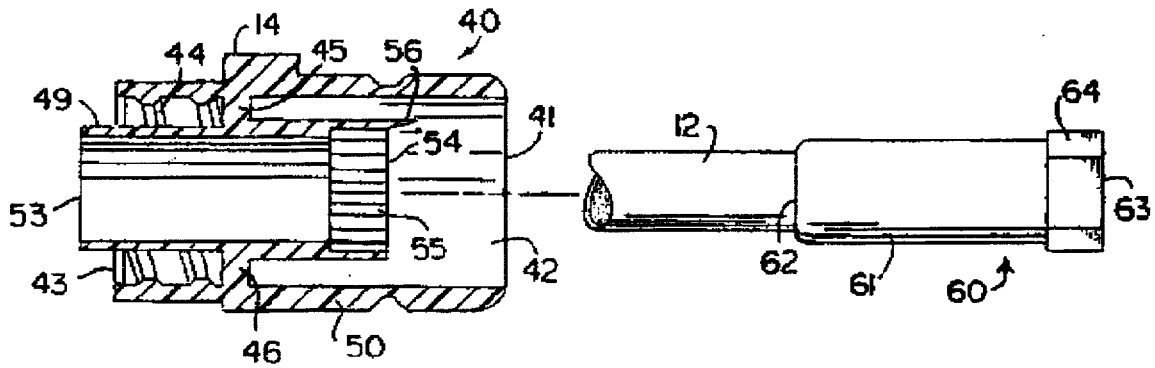

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–16 is confirmed.

Claim 2 is cancelled.

Claims 1, 17 and 19 are determined to be patentable as amended.

Claims 18 and 20–21, dependent on an amended claim, are determined to be patentable.

1. A surgical cutting instrument comprising:
    an inner tube having proximal and distal ends with a cutting means disposed proximate said distal end;
    an outer tube disposed in sheath-like fashion about said inner tube and having proximal and distal ends, said outer tube having a cutting window defined proximate its distal end in a position to permit said cutting means, when moving relative to said cutting window, to cut bodily tissue;
    drive means for cyclically moving said inner tube relative to said outer tube to thereby cyclically move said cutting means relative to said cutting window;
    a handpiece adapted to be grasped by a surgeon using said instrument; and
    an outer tube hub assembly secured at the proximal end of said outer tube and including means for selectively engaging said handpiece and preventing movement of said outer tube relative to said handpiece during said cyclical movement of said inner tube relative to said outer tube, said outer tube hub assembly including a positionally adjustable connection permitting selective angular positioning of said outer tube and said cutting window at plural discrete angular positions relative to said handpiece, *said outer tube hub assembly comprising a first hub member having a proximal end including said means for engaging said handpiece, and a second hub member secured to the proximal end of said outer tube, wherein said connection includes an angularly adjustable engagement between said first and second hub members without varying the relative longitudinal positions of the first hub member relative to the second hub member.*

17. A method for selectively orienting a cutting window relative to a handpiece in an endoscopic surgical cutting instrument of the type having an inner tube with a cutting edge at its distal end and movable within an outer tube having the cutting window at its distal end, said method comprising the steps of:
    providing a two-member hub assembly for said outer tube;
    connecting a first member of said hub assembly to said handpiece;
    connecting a second member of said hub assembly to the proximal end of said outer tube; and
    selectively engaging said first and second hub members in multiple alternative mutual angular orientations *without varying the relative longitudinal positions of the first member relative to the second member*;
    whereby said cutting window has a different angular orientation relative to the axis of said handpiece in each of said multiple angular orientations.

19. A surgical cutting instrument comprising:
    a longitudinally extending, rotatable inner tube having a proximal end and a distal end, said inner tube provided with a cutting means adjacent said distal end;
    an outer tube having an inside diameter substantially equal to the outside diameter of said inner tube, said outer tube having a proximal end and a distal end, the distal end of said outer tube being provided with a window opening adapted to enable said cutting means to cut tissue;
    rotation means for rotating said inner tube within said outer tube, said rotation means connected to the proximal end of said inner tube;
    an outer tube hub means connected to the proximal end of said outer tube;
    a handpiece for holding said outer tube hub means, said window opening having a predetermined angular position relative to said handpiece; and
    adjusting means for selectively varying the angular position of said window *at plural discrete angular positions* relative to said hub means.

* * * * *